(12) United States Patent
Kriksunov et al.

(10) Patent No.: US 8,298,198 B2
(45) Date of Patent: Oct. 30, 2012

(54) DUAL SPRAY CAN TOPICAL DELIVERY DEVICE

(75) Inventors: Leo B. Kriksunov, Glenside, PA (US); Ronni L. Robinson, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 624 days.

(21) Appl. No.: 12/426,349

(22) Filed: Apr. 20, 2009

(65) Prior Publication Data

US 2009/0264839 A1 Oct. 22, 2009

Related U.S. Application Data

(60) Provisional application No. 61/046,527, filed on Apr. 21, 2008.

(51) Int. Cl.
*A61M 35/00* (2006.01)

(52) U.S. Cl. ............ 604/289; 604/11; 604/310; 604/311

(58) Field of Classification Search .............. 604/11–14, 604/289, 310–311, 303–308; 401/190
See application file for complete search history.

(56) References Cited

U.S. PATENT DOCUMENTS

| | | | |
|---|---|---|---|
| 3,755,560 A | 8/1973 | Dickert et al. | |
| 3,802,604 A * | 4/1974 | Morane et al. | 222/83 |
| 4,254,105 A | 3/1981 | Fukuda | |
| 4,421,769 A | 12/1983 | Dixon et al. | |
| 4,960,764 A | 10/1990 | Figueroa, Jr. et al. | |
| 4,969,579 A | 11/1990 | Behar | |
| 5,260,065 A | 11/1993 | Mathur et al. | |
| 5,490,736 A * | 2/1996 | Haber et al. | 401/40 |
| 5,535,950 A | 7/1996 | Barriac et al. | |
| 6,284,234 B1 | 9/2001 | Niemiec et al. | |
| 6,316,021 B1 | 11/2001 | Gueret | |
| 6,347,899 B1 | 2/2002 | Vierboom | |
| 6,673,031 B2 * | 1/2004 | Mark | 604/1 |
| 6,811,341 B2 * | 11/2004 | Crane | 401/134 |
| 7,030,273 B1 | 4/2006 | Sun | |
| 7,189,760 B2 | 3/2007 | Erman et al. | |
| 2004/0116018 A1 | 6/2004 | Fenwick et al. | |
| 2004/0175343 A1 | 9/2004 | Osborne et al. | |
| 2005/0222320 A1 | 10/2005 | Torres et al. | |
| 2005/0232876 A1 | 10/2005 | Minga et al. | |
| 2007/0009467 A1 | 1/2007 | Keller | |
| 2008/0076697 A1 | 3/2008 | Heibel et al. | |

FOREIGN PATENT DOCUMENTS

| | | |
|---|---|---|
| EP | 713386 | 2/1995 |
| GB | 2328443 A | 2/1999 |
| GB | 2404588 A | 2/2005 |
| WO | WO 96/31194 | 10/1996 |
| WO | WO 98/03267 A | 1/1998 |
| WO | WO 01/37890 | 5/2001 |

OTHER PUBLICATIONS

International Cosmetic Ingredient Dictionary and Handbook, eds. Wenninger and McEwen, pp. 1626, 1650-1667, 1673-1686 & 1693-1697 (The Cosmetic, Toiletry, and Fragrance Assoc., Washington, D.C., 7$^{th}$ Edition, 1997—"ICI Handbook").
McCutcheon's Detergents and Emulsifiers, North American Edition, pp. 317-324 (1986).
Mezei & Gulasekharam, "Liposomes—A Selective Drug Delivery System for the Topical Route of Administration: Gel Dosage Form", Journal of Pharmaceutics and Pharmacology, vol. 34(1982), pp. 473-474.
Mezei, M., "Liposomes as a Skin Drug Delivery System", Topics in Pharmaceutical Sciences (D.Breimer and P. Speiser, eds.), Elsevier Science Publishers B.V., New York., 1985, pp. 345-358.
Niemiec et al., "Influence of Nonionic Liposomal Composition on Topical Delivery of Peptide Drugs into Pilosebaceous Units: An in Vivi Study Using the Hamster Ear Model". Pharmaceutical Research vol. 12 No. 8. pp. 1184-1188 (1995).
Sagarin, Cosmetics, Science and Technology, 2$^{nd}$ Edition, vol. 1, pp. 32-43 & 72-73 (1972).

* cited by examiner

*Primary Examiner* — Lynne Anderson
(74) *Attorney, Agent, or Firm* — Victor Tsu

(57) ABSTRACT

The present invention is directed to a delivery device and method for the sequential delivery of a topical pain relieving composition and an occluding composition. These two compositions are held in a single device that comprises at least two chambers for manual and or pressurized delivery of these compositions to the patient's skin.

22 Claims, No Drawings

DUAL SPRAY CAN TOPICAL DELIVERY DEVICE

CROSS REFERENCE TO RELATED APPLICATION

This application claims the benefit of priority of U.S. Provisional Applicatioon Ser. No. 61/046,527 filed Apr. 21, 2008.

BACKGROUND OF THE INVENTION

Topical therapeutic compositions have been traditionally used for pain relief of muscles, joints, as well as skin irritation and inflammation. In recent years, other types of pain, such as headache, have been treated using traditional topical active ingredients such as menthol. These types of products have been available as dial-on stick and cream types of dosage forms for application to the head, even though menthol is traditionally associated with topical treatment of muscle and joint pain. These types of treatments speak to the fact that pain experiences are extremely varied in the human population, and the sources, mechanisms and treatments are not completely understood by the medical profession and consumers of pain medications.

The use of topical therapeutic products can be improved through the use of occlusion of the product or active ingredient on the surface of the skin. In this case, occlusion has several advantages including the sealing of volatile components, prevention from having a topical therapeutic composition from rubbing off on surfaces such as clothes, as well as in the sealing of ingredients that emit unpleasant odors from the topical therapeutic composition. The occlusion of topical therapeutic compositions can also be utilized to facilitate delivery of the topical ingredient by having a consistent applied pressure of the topical ingredient through the epithelial layer of the skin. Occlusion, for instance by coating of the topical therapeutic composition applied to the skin by an adhesive patch, might also enhance the action of the active ingredients due to increase in skin permeability under the adhesive patch. Various means may be utilized in order to facilitate occlusion on the skin surface; including the addition of bandages, fabrics, hydrophobic liquid layers, tapes, impregnation of a topical into a patch.

Sprayed fabrics are a recently developed technology and enable the spraying of fibrous materials on the surface of an individual's body or onto a substrate, forming semi-permanent layers of fabric-like coatings. These are generally referred to as non-woven types of materials, such as shown in published U.S. Patent Application No. 2005/0222320 which comprises a sprayed fabric comprised of fibers, a binder and diluent. Spray fabrics may include ingredients that possess therapeutic or sensitizing properties; such as topical heating or warming agents. When such an agent is embedded in the composition of the sprayed fabric, it is trapped in its matrix structure and limits its availability for delivery on the surface of the skin, or subsequent absorption through the skin to underlying tissues. In addition, if an agent is impregnated into the sprayed fabric, it must be compatible with sprayed composition (i.e., the polymers, fibers, diluents, propellant and binders) in order to prevent degradation of the active ingredient of the functionality of the fabric. If the active ingredient is impregnated into the fabric, there is no real occlusion of the active ingredient upon delivery which can also lead to the potential for rubbing off on clothes, surfaces and emission of unpleasant odors.

Dual liquid delivery devices have been described in the art for delivering a variety of liquids, including the simultaneous delivery of multiple liquids. In U.S. Pat. No. 4,969,579, two liquids are combined upon simultaneous release from a dual chamber canister. In U.S. Pat. No. 5,535,950, teaches that a single trigger can be used to deliver two liquids from side-by-side pump pistons.

Many traditional topical pain relief compositions rely on one or more counter-irritants as the active ingredient. Counter-irritants function by providing a cold, hot, tingling, or other sensation that is believed to interfere with transmission of a pain signal to the brain, providing temporary lessening of the perception of sore muscles or aching joints. For example, Ben Gay Ultra Strength pain relieving cream contains such counter-irritant active ingredients as menthol (10%), camphor (4%), and methyl salicylate (30%), and has an onset of sensation within about 3 minutes with about a 90-minute duration of sensation.

Cooling agents have been disclosed in the prior art for use as sensates, such as disclosed in U.S. Pat. No. 7,189,760, wherein a substantially pure compound and method of preparing an ethyl ester of N-[[5-methyl-2-(1-methylethyl)cyclohexyl]carbonyl]glycine is shown. This material is described as having substantially high physiological cooling activity.

Similarly, U.S. Pat. No. 7,030,273 discloses additional cooling agents. In this patent, N-alkoxyalkyl substituted-2,3-dimethyl-2-isopropylbutyramides compounds are demonstrated to have physiologic cooling effects.

The invention described herein improves the delivery of a topical therapeutic agent and avoids incompatibility issues associated with fiber impregnation.

SUMMARY OF THE INVENTION

The present invention described herein is a method and a device having a topical pain relieving composition that is delivered by means which are convenient and provide for occlusion of the composition. In the present invention, the occlusion is provided by a sprayed polymer, sprayed polymer complex, or sprayable fabric. In one embodiment, the method of improving the action, efficacy and stability of the topical through occlusion using a sprayed fabric or polymer complex is presented.

In addition, other advantages are realized with the use of the present invention, including: application of a topical without oiliness or greasiness; conservation of the topical therapeutic composition since it will not rub off on external surfaces (i.e. clothes); sealing of the offending odor that can be associated with some pain relieving topical products; as well as targeted delivery of the topical.

In one embodiment, a topical therapeutic composition is delivered from one chamber of a multi-chamber container and a sprayed fabric or polymer complex is delivered sequentially from a separate pressurized chamber within the container in order to occlude the topical application.

Advantageously, separate compartments for the therapeutic agent and the occluding composition provide for better stability and decreased amount of interactions between these compositions while in storage, thus simplifying the composition mixture design and also increasing the shelf life of the product.

In one aspect of the invention, the spray device provides for the delivery of a therapeutic agent to the skin that is occluded and protected by a conformal protective coating, thus forming a medicated patch. The spray application of the medicated patch results a patch which is conforming to any area of the body and exhibits good adhesion even in the areas subject to bending and stretching of the skin, such areas of elbows and knees. The occluding component of the patch, being substantially inert, provides for protection of the underlying topical therapeutic composition.

DETAILED DESCRIPTION OF THE INVENTION

The first part of this invention includes the delivery of a topical therapeutic composition from the spray device; wherein the topical therapeutic agent is in the form of a liquid, suspension, cream, emulsion or ointment. The topical therapeutic agent is delivered from a variety of means depending on the vehicle form which may include a manual aerosol pump spray or a pressurized pump spray, as in the case of a liquid. In one embodiment, the spray may also be delivered via a pressurized pump spray chamber further containing a propellant.

In an embodiment where the topical vehicle is a viscous suspension, cream or emulsion, then a manual pump can deliver a fixed amount of the topical therapeutic agent with a single or multiple depressions of the pump lever. Since the delivery of the topical therapeutic agent and the sprayed fabric is performed in a sequential order, the means of releasing the topical and the sprayed fabric can be performed using a single lever or button. In this embodiment, partial depression of the pump lever or button first delivers the topical therapeutic agent to the targeted skin area, accompanied by a physical stop of the pump lever, wherein additional compression of the pump lever releases the sprayed fabric on top of the topical.

As used herein, "topical therapeutic composition" refers to a composition used for application to the skin that is intended to provide itch or pain relief for a period of time. This may include compositions using heating active ingredients or sensate, cooling active ingredients or sensates, numbing or tingling sensates, counter-irritants, or topical analgesics.

The "occluding composition" as used herein described refers to a composition used for application following the delivery of the topical therapeutic composition which occludes and seals the topical therapeutic composition on the skin.

As used herein, "sequential delivery" refers to the method of delivery wherein the topical therapeutic composition containing therapeutic agents is delivered first to a given area of the patient's skin, and the occluding composition is delivered thereafter, being delivered substantially on top of the topical therapeutic composition.

Description of the Delivery Device

The topical therapeutic composition and sprayed fabric can be housed in a variety of different container and packaging configurations in order to deliver the two ingredients in a sequential manner.

In one embodiment of the spray delivery device, the two components are delivered to the skin surface through two separate orifices, both of which are manually controlled with two separate buttons or release levers. In this embodiment, the initial delivery of the topical can first be achieved by application through one orifice and one button or release lever and the delivery of the occluding composition (i.e. sprayed fabric) is sequentially performed by manual application through a second button or release lever. In this embodiment, the consumer is directed to apply these components in sequence to the skin through written instructions. The consumer or patient consequently has the option of utilizing the topical therapeutic composition with or without the addition of the occluding composition.

In the embodiment where two orifices are used to deliver the two compositions, the written instructions can also be accompanied by visual cues that instruct the consumer to deliver the ingredients in sequence. These include but are not limited to vertical positioning of the two pump delivery orifices, wherein the topical orifice is higher or lower than the occluding composition. Other means include varying the sizes of the pump buttons, release levers or delivery orifices including varying the height, length or width. The two orifices, pump buttons or release levers may be color codes or numbered, wherein the topical therapeutic composition comprises a "1" or "+" and the occluding composition comprises a "2" or "++". In this embodiment the device comprises two chambers, one containing the topical therapeutic composition and one the occluding composition, and each having its own separate delivery orifice. The two chambers are connected to form a single delivery device.

In one embodiment, the delivery device comprises multiple chambers, wherein one chamber contains the topical therapeutic composition and a second chamber contains an occluding composition, and the two compositions are delivered to the skin in sequence by means of a single orifice with a single spray button. In this embodiment, a valve is incorporated into the delivery orifice that controls the sequential delivery. In this embodiment, the compression of the delivery button, lever or nozzle allows for a metered dose delivery of the topical therapeutic composition followed by a metered dose of the occluding composition. In one embodiment, this sequential dosing is achieved through a check valve or separator which allows for delivery through a single compression of the button or lever and a single orifice. In one embodiment, there is a dual separated orifice wherein the sequential delivery of the topical therapeutic composition and the occluding composition is achieved through a single compression of the delivery lever. In one embodiment, the device in this embodiment incorporates a timed release valve, which is operated by a spring-loaded timing mechanism. Other means of delivering the topical therapeutic compositions and the occluding composition include the incorporation of a pressure actuated flap, wherein the pressure from the topical is released under a different pressure from the occluding composition, and the pressure difference actuates the flap.

In one embodiment, the delivery device comprises multiple chambers, wherein one chamber contains the topical therapeutic composition and a second chamber contains an occluding composition, and the two compositions are delivered to the skin in sequence by means of two separate orifices with a single spray button controlling sequential operation of both orifices, wherein (i) the topical therapeutic composition is delivered first and the occluding composition is delivered thereafter to cover the topical therapeutic composition; or (ii) the delivery of the occluding composition is initiated with a delay after the delivery of the topical therapeutic composition has already started but still continues; or (iii) the delivery of the occluding composition is initiated simultaneously with the delivery of the topical therapeutic composition. In the (ii) and (iii) scenarios above, to ensure that the occluding composition covers the already deposited topical therapeutic composition, the spray orifices are directed towards areas which are adjacent but separate spatially, and upon moving the spray deposition system over the skin, the topical therapeutic composition is deposited first, and the occluding composition is deposited at least partially on top of the topical therapeutic composition.

In one embodiment, the topical therapeutic composition and the occluding composition are delivered through a manual pump. In a separate embodiment, the topical therapeutic composition is delivered through a manual compression of the delivery lever and the occluding composition is delivered by a compressed propellant. In another embodiment, both chambers contain compressed propellants. In a separate embodiment, a third chamber contains compressed propellant that is used to deliver both the topical therapeutic composition and the occluding composition.

Suitable propellants for use the present invention include but are not limited to mixtures of volatile hydrocarbons such as propane, n-butane and isobutane; dimethyl ether (DME), methyl ethyl ether; nitrous oxide, carbon dioxide, hydrofluoroalkanes (HFA): either HFA 134a (1,1,1,2-tetrafluoroethane) or HFA 227 (1,1,1,2,3,3,3-heptafluoropropane) and mixtures thereof.

The outer spray cannister has one or more chambers or portions. The chambers can be constructed of various materials including but not limited to steel, tin plate, aluminum, copper, polypropylene, polyethylene, or combinations or alloys thereof. In the case of a compressed sprayed occluding composition, the delivery device is comprised of an orifice, actuator, gasket, spring and diptube which extends down into the chamber containing the occluding composition.

Description of Topical Therapeutic Composition

The topical therapeutic compositions of the present invention can be prepared in a number of forms for application to the skin (topical application) of a patient. For example, the composition can be applied in a gel, cream, ointment, liquid, spray liquid, paint-/brush-on preparation, solidifying emulsion or cream (i.e. facial mask), aerosol, powder, oil, balm, salve, or adhesive bandage. The topical therapeutic compositions of the present invention can be in the form of meltable solids, semi-solids, solutions, suspensions, or emulsions. In addition, the composition can be impregnated on a bandage, hydrocolloid dressing, treatment patch or on cloth wipe products. In one embodiment, the topical therapeutic composition can have resistance to moisture and subsequent washing off from the skin.

Suitable external analgesics include but are not limited to those disclosed in the Tentative Final Monograph for External Analgesic Drug Products for over-the-counter human use, U.S. Federal Register Vol. 48, No. 27, Feb. 28, 1983. These monographed external analgesics include counter-irritants that produce redness, for example, Allyl isothiocryanate 0.5-5%, Methyl salicylate 10-60%, and Turpentine oil 6-50%; Irritants that produce cooling, for example, Camphor>3% to 11%, or Menthol 1.25-16%; Irritants that produce vasodilation, for example Histamine dihydrochloride 0.025-0.10%, or Methyl nicotinate 0.25-1%; and irritants that do not produce redness, for example, Capsaicin 0.025-0.25%, Capsicum containing 0.025-0.25% capsaicin, or Capsicum oleoresin containing 0.025-0.25% capsaicin.

Suitable anti-itch agents include corticosteroids such as but not limited to hydrocordisone and flurandrenolide as well as herbal agents such as but not limited to camomille, tea tree oil and calendula. Suitable topical antihistamines for use in the therapeutic composition include but are not limited to doxepin. In one embodiment the therapeutic composition comprises a pain relieving active ingredient as well as an anti-itch agent. In another embodiment the therapeutic composition comprises a first pain relieving active ingredient and the occluding composition comprises an anti-itch agent.

Suitable non-monograph cooling sensates are selected from the group including but are not limited to [(−)-isopulegol, (2S)-3-(1-menthoxy)propane-1,2-diol, "Frescolat MGA"/menthone glycerin acetal, "Frescolat ML"/menthyl lactate, "WS-14"/N-t-butyl-p-menthane-3-carboxamide, "WS-23"/2-Isopropyl-N,2,3-trimethylbutyramide, WS-12/ N-(4-methoxyphenyl)-p-menthane-3-carboxamide, "WS-3"/N-Ethyl-p-menthane-3-carboxamide, and "WS-5"/Ethyl 3-(p-menthane-3-carboxamido)acetate].

In other embodiments, the topical therapeutic compositions can also include transdermally delivered drug substances, including but not limited to pain reliving drugs, anti-infective drugs, heart disease targeting drugs, anti-depression drugs, hormonal supplements and drugs, addiction treatment drugs, such as nicotine or nicotine analogs, central nervous system treatment drugs, diabetes treatment drugs, or any other drugs or active agents for treating disease or alleviating symptoms of a disease or a condition of the patient. In one embodiment the pain relieving drug includes but is not limited to ketoprofen, ibuprofen, diclofenac, niflumic acid, felbinac, and piroxicam.

In other embodiments, the topical therapeutic compositions can also include penetration enhancers, which increase the skin permeability towards the drugs or active agents contained in the topical therapeutic composition.

In certain embodiments, the topical therapeutic compositions of the present invention comprise a dermatologically acceptable carrier. Such a carrier is suitable for topical use that is compatible with the active ingredients described herein. An effective and safe carrier varies from about 50% to about 99% by weight of the compositions of this invention, more preferably from about 75% to about 99% of the compositions and most preferably from about 75% to about 95% by weight of the compositions.

The topical therapeutic compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Topical therapeutic compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook") contains numerous examples of suitable materials.

A lotion can be made from a solution containing an emollient. Lotions typically comprise from about 1% to about 20% (e.g., from about 5% to about 10%) of an emollient(s) and from about 50% to about 90% (e.g., from about 60% to about 80%) of water. Another type of product that may be formulated from a solution containing an emollient is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution containing an emollient is an ointment. An ointment can comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical therapeutic compositions useful in the present invention can be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multi-phase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical therapeutic compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical therapeutic compositions of the present invention can also be formulated into a solid composition (e.g., a wax-based stick, soap bar composition, powder, or a wipe containing powder).

Liposomal compositions are also useful compositions of the subject invention. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473-474, or a modification thereof. Epidermal lipids of suitable composition for forming liposomes may be substituted for the phospholipid. The liposome preparation may then incorporated into one of the above carriers (e.g., a gel or an oil-in-water emulsion) in order to produce the liposomal composition. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345-358, PCT Patent Application No. WO96/31194, Niemiec, et al., 12 Pharm. Res. 1184-88 (1995), and U.S. Pat. No. 5,260,065.

In one-embodiment, the liposome is non-ionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome comprises glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical therapeutic composition in an amount, based upon the total volume of the composition, of from about 10 mg/ml to about 100 mg/ml such as from about 15 mg/ml to about 50 mg/ml.

The topical therapeutic compositions useful in the subject invention may contain, in addition to the aforementioned components, a wide variety of additional oil-soluble materials and/or water-soluble materials conventionally used in compositions for use on skin, hair, and nails at their art-established levels.

Various other materials may also be present in the compositions useful in the subject invention. These include adsorbants, humectants, proteins and polypeptides, preservatives and an alkaline agent. Examples of such agents are disclosed in the ICI Handbook, pp. 1650-1667.

The compositions of the present invention may also comprise chelating agents (e.g., EDTA) and preservatives (e.g., parabens). Examples of suitable preservatives and chelating agents are listed in pp. 1626 and 1654-55 of the ICI Handbook. In addition, the topical therapeutic compositions useful herein can contain conventional cosmetic adjuvants, such as dyes, opacifiers (e.g., titanium dioxide), pigments, and fragrances.

In another embodiment, the active ingredient(s) are incorporated into a cream or lotion vehicle such as for example the type disclosed in U.S. Pat. No. 6,284,234. A preferred embodiment comprises a) from about 1 percent to about 10 percent of a nonionic lipid; b) from about 75 percent to about 98 percent of a vehicle solution comprised of water or a mixture of water and a hydrophilic compound and a second vehicle component comprised of an alcohol, a polyol, or mixtures thereof, and c) an effective amount of the active ingredient(s).

Delivery of Occluding Composition

The occluding composition of the present invention may be delivered as a sprayable fabric, cross-linked polymer, or polymer which is polymerizing or cross-linking upon spraying. In one embodiment, the occluding composition is a pumpable or sprayable solution, suspension, or emulsion that forms a continuous or discontinuous coating, an adhesive film, or a nonwoven fabric when sprayed onto the skin. Spraying fabrics are described, for example, in published U.S. Patent Application 2005/0222320.

Occluding composition can also comprise polymers that solidify upon spraying due to drying or UV curing, or cross-link on contact with moisture present in the air, or cross-link on contact with oxygen present in the air. Examples include cyanoacrylates, such as 2-octyl cyanoacrylate, which quickly polymerize on contact with moisture present in the air.

In another embodiment, the occluding composition is sprayed from a container having multiple, preferably two, compartments separately storing the polymer and the cross-linking agent, and the occluding composition is formed by mixing the polymer and the cross-linking agent during spraying, as known in the art.

In one embodiment, the occluding composition forms a porous coating on the skin, to provide for skin breathability. In one such embodiment, the occluding composition comprises a mixture of porous particles with a cross-linkable polymer, with the porous particles being embedded into the coating formed by the occluding composition. The coating is then rendered more breathable due to presence of porous particles providing for air and moisture permeability. In another embodiment, the occluding composition forms a micro-porous coating due to micro-bubbles present or formed in the occluding composition during application.

In one embodiment, an ingredient(s) which delivers a sensory cue is incorporated into a polymer-containing solution, suspension, or emulsion, which forms a solid mesh or entrapment upon application which adheres to the skin and solidifies.

In one embodiment, the occluding composition may comprise an identifier which demonstrates that it is different from the topical therapeutic composition. This identifier may be in the form of sensory cue such as a fragrance, or a color which is different from that of the topical therapeutic composition. In one embodiment, the occluding composition contains an identifier such as reflective flakes, colored microbeads, or fibers which demonstrate that the occluding composition is different from the topical therapeutic composition.

In one embodiment, the occluding composition substantially covers the topical therapeutic composition. As used herein, "substantially covers" includes coating or covering at least 75 percent, e.g. at least about 90 percent; e.g. at least about 95 percent of the surface area of the first applied topical therapeutic composition. In another embodiment, the occluding composition covers at least 100% of the topical therapeutic composition on the skin, or completely covers the topical therapeutic composition on the skin. In yet another embodiment, the occluding composition overcoats the topical therapeutic composition on the skin, extending beyond the area where the topical therapeutic composition is applied, approximately uniformly extending over the area coated with the topical therapeutic composition in all directions, e.g. coating the area that is approximately 110% of the topical therapeutic composition area; e.g. coating the area that is approximately 150% of the topical therapeutic composition area. In one embodiment the therapeutic composition and the occluding composition are applied in circular patterns, whereas the occluding composition overlaps the therapeutic composition by at least 2 mm, or about at least 5 mm, or about at least 10 mm.

In one embodiment, the topical therapeutic composition, the occluding composition or both have the ability to minimize wash-off, or wash-off resistance. Compositions that exhibit wash-off resistance are known. For example, published U.S. Patent Application No. 2005/0232876 describes skin care compositions that are useful as cosmetic, protective and therapeutic dermatological compositions that exhibit smoothness and water resistance when applied to the skin. In examples, the contact angle of water on films of the inventive compositions was measured to show the water resistant nature of these mixtures. Contact angle is a measure of the surface wettability and is described in Test Method ASTM D5725-99.

In one embodiment the occluding composition comprises a non-toxic volatile solvent which is dried from the occluding composition upon application. Suitable solvents include but are not limited to ethanol, methanol, and isopropanol, In one embodiment, the composition is worn by the user for at least 1 hour, or at least 2 hours, or at least 4 hours or at least 8 hours.

Delivery Sequence

In one embodiment, substantially all of the topical therapeutic composition is applied to the skin first and then substantially all of the occluding composition is applied to the skin substantially over the topical therapeutic composition.

In another embodiment, both topical therapeutic composition and occluding composition are initially sprayed simultaneously on the adjacent areas on the skin. Then the spraying nozzles are moved to expand the area of coverage so that the occluding composition covered area follows the topical therapeutic composition application area and immediately overcoats the topical therapeutic composition. The spraying of the topical therapeutic composition is turned off first while the occluding composition is still spraying to provide complete coverage the topical therapeutic composition application area.

In both delivery methods described above, each area of the skin is sequentially coated by the topical therapeutic composition and then by the occluding composition.

In one embodiment the therapeutic composition comprises an additional crosslinking agent which induced a polymer within the occluding composition to crosslink upon contact with the therapeutic composition. Suitable crosslinking agents include but are not limited to boric acid, glycerol, polyethylene glycol and glycerol monolaurate.

We claim:

1. A topical delivery device comprising a canister having a first chamber that contains a topical therapeutic composition comprising at least one active ingredient; and a second chamber containing an occluding composition; wherein said delivery device sequentially delivers the topical therapeutic composition and the occluding composition, and wherein the topical composition and the occluding composition are metered through a valve and sequentially delivered through a single nozzle.

2. The topical delivery device according to claim 1, wherein the active ingredient provides pain relief for a period of time when applied topically.

3. The topical delivery device of claim 1, wherein the occluding composition produces a sprayed fabric or a sprayed polymer after being dispensed from the device.

4. The topical delivery device of claim 1, wherein the active ingredient of the topical therapeutic composition is selected from the group consisting of heating agents, cooling agents, topical analgesics, counter-irritants, heating sensates, cooling sensates, and tingling sensates.

5. The topical delivery device of a claim 1, wherein the occluding composition contains an identifier relative to the topical therapeutic composition.

6. The topical delivery device of claim 1, wherein the occluding composition overcoats the topical therapeutic composition.

7. The topical delivery device of claim 6, wherein the area coated by the occluding composition is approximately 110% of the topical therapeutic composition area.

8. The topical delivery device of claim 1, wherein the topical therapeutic composition comprises a first pain relieving active ingredient and a second anti-itch active ingredient.

9. The topical delivery device of claim 1, wherein the occluding composition comprises an anti-itch agent.

10. The topical delivery device of claim 1, wherein the topical therapeutic composition comprises a cross-linking agent.

11. A topical delivery device comprising a canister having a first chamber that contains a topical therapeutic composition comprising at least one active ingredient; and a second chamber containing an occluding composition; wherein said delivery device sequentially delivers the topical therapeutic composition and the occluding composition, and wherein the topical therapeutic composition is dispensed from the device by activating a first release button and the occluding composition is dispensed from the device by activating a second release button.

12. The topical delivery device according to claim 11, wherein the active ingredient provides pain relief for a period of time when applied topically.

13. The topical delivery device of claim 11, wherein the occluding composition produces a sprayed fabric or a sprayed polymer after being dispensed from the device.

14. The topical delivery device of claim 11, wherein the active ingredient of the topical therapeutic composition is selected from the group consisting of heating agents, cooling agents, topical analgesics, counter-irritants, heating sensates, cooling sensates, and tingling sensates.

15. The topical delivery device according to claim 11, wherein the occluding composition contains an identifier relative to the topical therapeutic composition.

16. The topical delivery device of claim 11, wherein the occluding composition overcoats the topical therapeutic composition.

17. The topical delivery device of claim 16, wherein the area coated by the occluding composition is approximately 110% of the topical therapeutic composition area.

18. The topical delivery device of claim 11, wherein the topical therapeutic composition comprises a first pain relieving active ingredient and a second anti-itch active ingredient.

19. The topical delivery device of claim 11, wherein the occluding composition comprises an anti-itch agent.

20. The topical delivery device of claim 11, wherein the topical therapeutic composition comprises a cross-linking agent.

21. A pain relieving topical treatment device comprising a canister having a first chamber that contains a pain relieving topical therapeutic composition comprising at least one pain relieving active ingredient; and a second chamber containing an occluding composition; wherein said device sequentially dispenses the pain relieving topical therapeutic composition and the occluding composition, and wherein the topical composition and the occluding composition are metered through a valve and sequentially delivered through a single nozzle.

22. A pain relieving topical treatment device comprising a canister having a first chamber that contains a pain relieving topical therapeutic composition comprising at least one pain relieving active ingredient; and a second chamber containing an occluding composition; wherein said device sequentially dispenses the pain relieving topical therapeutic composition and the occluding composition, and wherein the topical therapeutic composition is dispensed from the device by activating a first release button and the occluding composition is dispensed from the device by activating a second release button.

* * * * *